(12) United States Patent
Persat

(10) Patent No.: US 8,858,461 B2
(45) Date of Patent: Oct. 14, 2014

(54) TISSUE SAMPLING TOOL, IN PARTICULAR FOR ADIPOSE TISSUE

(76) Inventor: Jean-Charles Persat, Geneva (CH)

( * ) Notice: Subject to any disclaimer, the term of this patent is extended or adjusted under 35 U.S.C. 154(b) by 78 days.

(21) Appl. No.: 13/291,194

(22) Filed: Nov. 8, 2011

(65) Prior Publication Data

US 2012/0130274 A1    May 24, 2012

(30) Foreign Application Priority Data

Nov. 19, 2010   (FR) ...................... 10 59533

(51) Int. Cl.
*A61B 10/00* (2006.01)
*A61B 17/3207* (2006.01)
*A61B 10/02* (2006.01)

(52) U.S. Cl.
CPC ......... *A61B 10/0275* (2013.01); *A61B 10/0283* (2013.01); *A61B 17/320783* (2013.01)
USPC ......................................... 600/562; 600/564

(58) Field of Classification Search
CPC ....................................................... A61B 5/00
USPC ................................. 600/562, 564
See application file for complete search history.

(56) References Cited

U.S. PATENT DOCUMENTS

| | | | | |
|---|---|---|---|---|
| 3,081,770 A | * | 3/1963 | Hunter | 600/431 |
| 3,606,878 A | * | 9/1971 | Kellogg | 600/566 |
| 4,011,869 A | * | 3/1977 | Seiler, Jr. | 604/22 |
| 4,111,207 A | * | 9/1978 | Seiler, Jr. | 606/171 |
| 4,314,560 A | * | 2/1982 | Helfgott et al. | 606/171 |
| 4,340,066 A | * | 7/1982 | Shah | 600/562 |
| 4,530,356 A | * | 7/1985 | Helfgott et al. | 606/171 |
| 4,603,694 A | * | 8/1986 | Wheeler | 606/171 |
| 4,651,753 A | * | 3/1987 | Lifton | 600/564 |
| 4,660,267 A | * | 4/1987 | Wheeler | 29/437 |
| 4,702,260 A | * | 10/1987 | Wang | 600/566 |
| 4,781,186 A | * | 11/1988 | Simpson et al. | 606/171 |
| 4,811,734 A | * | 3/1989 | McGurk-Burleson et al. | 606/174 |
| 4,850,354 A | * | 7/1989 | McGurk-Burleson et al. | 606/170 |
| 4,867,157 A | * | 9/1989 | McGurk-Burleson et al. | 606/170 |
| 4,983,179 A | * | 1/1991 | Sjostrom | 606/180 |
| 5,047,008 A | * | 9/1991 | de Juan et al. | 604/22 |
| 5,059,204 A | * | 10/1991 | Lawson et al. | 606/171 |

(Continued)

FOREIGN PATENT DOCUMENTS

| | | |
|---|---|---|
| DE | 100 49 813 | 4/2002 |
| EP | 0 800 794 | 10/1997 |

(Continued)

*Primary Examiner* — Rene Towa
*Assistant Examiner* — May Abouelela
(74) *Attorney, Agent, or Firm* — Clark & Brody

(57) ABSTRACT

A tissue-sampling tool is made in the form of a tube presenting an inside face of circular section and an outside face of circular section, the tube having a blunt distal end and at least one sampling orifice extending symmetrically relative to a transverse plane and to a longitudinal plane. The orifice is peripherally bordered by two transverse borders that are symmetrical relative to the transverse plane and that are connected to two longitudinal borders that are symmetrical relative to the longitudinal plane. Each transverse border possesses a cutting edge situated at the intersection between said borders and the inside face, each transverse border cooperating with the inside face to form a cutting angle lying in the range 6° to 18°. The longitudinal borders have a cup-shape relative to the transverse borders, with a profile in the longitudinal plane that is different from the profile of the transverse borders.

8 Claims, 2 Drawing Sheets

(56) References Cited

U.S. PATENT DOCUMENTS

| | | | | |
|---|---|---|---|---|
| 5,061,238 A * | 10/1991 | Shuler | | 604/22 |
| 5,106,364 A * | 4/1992 | Hayafuji et al. | | 604/22 |
| 5,284,472 A * | 2/1994 | Sussman et al. | | 604/22 |
| 5,335,671 A * | 8/1994 | Clement | | 600/566 |
| 5,409,013 A * | 4/1995 | Clement | | 600/566 |
| 5,458,112 A * | 10/1995 | Weaver | | 600/566 |
| 5,474,532 A * | 12/1995 | Steppe | | 604/22 |
| 5,505,210 A * | 4/1996 | Clement | | 600/566 |
| 5,527,332 A * | 6/1996 | Clement | | 606/171 |
| 5,693,011 A * | 12/1997 | Onik | | 604/22 |
| 5,733,297 A * | 3/1998 | Wang | | 606/167 |
| 5,782,849 A * | 7/1998 | Miller | | 606/159 |
| 5,797,907 A * | 8/1998 | Clement | | 606/49 |
| 5,843,111 A * | 12/1998 | Vijfvinkel | | 606/171 |
| 5,873,886 A * | 2/1999 | Larsen et al. | | 606/180 |
| 5,879,365 A * | 3/1999 | Whitfield et al. | | 606/180 |
| 5,928,161 A * | 7/1999 | Krulevitch et al. | | 600/564 |
| 6,027,514 A * | 2/2000 | Stine et al. | | 606/159 |
| 6,361,504 B1 * | 3/2002 | Shin | | 600/562 |
| 6,572,578 B1 * | 6/2003 | Blanchard | | 604/22 |
| 6,709,408 B2 * | 3/2004 | Fisher | | 600/570 |
| 6,743,245 B2 * | 6/2004 | Lobdell | | 606/171 |
| 7,637,872 B1 * | 12/2009 | Fox | | 600/562 |
| 7,670,299 B2 * | 3/2010 | Beckman et al. | | 600/566 |
| 7,693,567 B2 * | 4/2010 | Tsonton et al. | | 600/411 |
| 7,708,751 B2 * | 5/2010 | Hughes et al. | | 606/172 |
| 7,711,407 B2 * | 5/2010 | Hughes et al. | | 600/417 |
| 7,828,745 B2 * | 11/2010 | McAlister et al. | | 600/566 |
| 2002/0193705 A1 * | 12/2002 | Burbank et al. | | 600/562 |
| 2003/0078609 A1 * | 4/2003 | Finlay et al. | | 606/171 |
| 2003/0236471 A1 * | 12/2003 | Fisher | | 600/573 |
| 2005/0090765 A1 | 4/2005 | Fisher | | |
| 2007/0161925 A1 * | 7/2007 | Quick et al. | | 600/564 |
| 2007/0213630 A1 * | 9/2007 | Beckman et al. | | 600/562 |

FOREIGN PATENT DOCUMENTS

| | | |
|---|---|---|
| EP | 1 092 515 | 4/2001 |
| EP | 2 140 820 | 1/2010 |
| FR | 2 942 410 | 8/2010 |
| WO | 01/00100 | 1/2001 |

* cited by examiner

TISSUE SAMPLING TOOL, IN PARTICULAR FOR ADIPOSE TISSUE

FIELD OF THE INVENTION

The present invention relates to the general technical field of sampling adipose tissue of the human body by using sampling tools also known as cannulas or needles.

The invention finds particularly advantageous applications in the field of certain cell therapy treatments that have recourse to the stem cells of the sampled adipose tissue, in the field of tissue autografts in plastic surgery (breast, face, hands, . . . ) or for reconstructive surgery to complement loss of material (bone), or indeed in the field of liposuction in adipose zones.

BACKGROUND OF THE INVENTION

In the state of the art, it is known to sample adipose tissue using a cannula made in the form of a needle or a tube that presents an internal bore of circular section and an outside face of circular section. The cannula generally includes an atraumatic blunt distal end for insertion into the tissue and a proximal end for connection with a gripper element. The tube is arranged to include one or more adipose tissue sampling orifices that communicate with the internal bore of the cannula, which bore is generally connected to a suction source.

In practice, sampling adipose tissue leads to tissue lesions or to tissue being torn. Sample-taking in that way frequently gives rise to severe post-sampling inflammatory phenomena and can generate extensive bleeding. In addition, sample-taking in that way presents a yield that is relatively low with the tissue that is taken being of poor quality.

In the field of catheters, document DE 100 49 813 discloses a catheter for ablation of a calcified aortic valve. At its distal end, the catheter is provided with an ablation system comprising a tube having an inside face of circular section and an outside face of circular section. The tube has a sampling orifice bordered by a cutting edge. A cutting tool is movably mounted inside the tube and presents an opening that defines a cutting edge. Such an ablation system is of complex design and it is complex to use, in particular because of the presence of a movable cutting tool. Furthermore, such an ablation system does not enable sample-taking to be precise and of good quality, by virtue of the very principle of the ablation system.

OBJECT AND SUMMARY OF THE INVENTION

The present invention seeks to remedy the drawbacks of the prior art by proposing a sampling tool that minimizes the tearing effect on adipose tissue while also enabling cells to be taken in collections of given size and of good quality.

Another object of the invention is to provide a tool for sampling adipose tissue that is of simple design, enabling the act of transcutaneous sample-taking to be painless and fast.

To achieve such an object, the invention provides a tissue-sampling tool made in the form of a tube presenting an inside face of circular section and an outside face of circular section, the tube having a blunt distal end and at least one sampling orifice extending symmetrically relative to a transverse plane and to a longitudinal plane, the orifice being peripherally bordered by two transverse borders that are symmetrical relative to the transverse plane and that are connected to two longitudinal borders that are symmetrical relative to the longitudinal plane.

According to the invention,
each transverse border possesses a cutting edge situated at the intersection between said borders and the inside face, each transverse border co-operating with the inside face to form a cutting angle lying in the range 6° to 18°; and
the longitudinal borders are arranged to have a cup-shape relative to the transverse borders, with a profile in the longitudinal plane that is different from the profile of the transverse borders.

Furthermore, the tool of the invention may also present one or more of the following additional characteristics in combination:
the cutting edge of each transverse border comprises two converging segments that are connected together by a connection segment presenting a profile that is different from the profile of the converging segments;
the cutting edge of each transverse border comprises two converging segments connected together by a rounded connection segment;
each transverse border presents a plane profile in the longitudinal plane;
each transverse border presents a convex profile in the longitudinal plane;
each transverse border is extended in the longitudinal direction and on either side of the longitudinal plane by a tapering zone;
the profile of each longitudinal border presents two converging curved segments that are connected together by a straight segment; and
the profile of each longitudinal border presents two converging curved segments that are connected together by a rounded segment.

BRIEF DESCRIPTION OF THE DRAWINGS

Various other characteristics appear from the following description made with reference to the accompanying drawings that show embodiments of the invention as non-limiting examples.

MORE DETAILED DESCRIPTION

Figure 1:
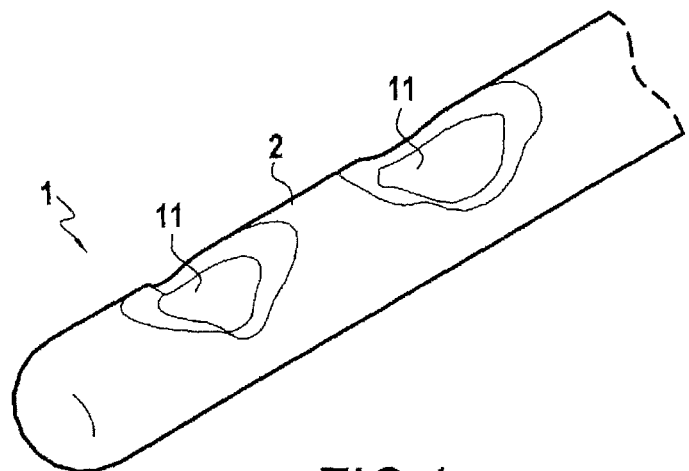
FIG. 1 is a perspective view of an embodiment of a sampling tool in accordance with the invention.

As can be seen more precisely from the figures, the invention relates to a sampling tool 1 such as a cannula or a needle in the broad sense that has been adapted to sampling adipose tissue in the human body. The sampling cannula 1 comprises a tubular needle or tube 2 that is semirigid, and that presents a longitudinal axis of symmetry X. Advantageously, the tube 2 is made of metal, of stainless steel.

The tube 2 has a closed hemispherical or rounded distal end 3. The tube 2 thus presents an atraumatic blunt end 3. At its end remote from the distal end 3, the tube 2 has a proximal end 4 for grasping, e.g. connected to a sampling device (not shown) of any known type. For example, such a sampling device may be a syringe or a suction system of the type including a vacuum source.

The tube 2 presents an internal channel or bore 6 defined by the tubular inside face 7 that presents an inside right cross-section that is preferably circular. The tube 2 also presents a tubular outside face 8 that presents an outside right cross-section that is preferably circular. The tube 2 thus presents a wall of constant thickness e.

The sampling cannula 1 of the invention also includes at least one sampling opening or orifice 11, and in the example shown it includes two of them. Each sampling orifice 11 is a through opening providing communication between the inside and outside faces 7 and 8 of the tube 2.

Each sampling orifice 11 extends symmetrically relative to a transverse plane T and to a longitudinal plane L. The transverse plane T is perpendicular to the longitudinal axis X and to the longitudinal plane L containing the longitudinal axis X.

Each sampling orifice 11 is bordered at its periphery by two transverse borders 13 that extend symmetrically relative to the transverse plane T. These two transverse borders 13 are connected to two longitudinal borders 14 that extend symmetrically relative to the longitudinal plane L. Each transverse border 13 extends symmetrically from the longitudinal plane L away therefrom. Each longitudinal border 14 extends symmetrically from the transverse plane T away therefrom so as to be connected at each end to respective transverse borders 13. Thus, around its entire periphery, each sampling orifice 11 is provided with two transverse borders 13 and two longitudinal borders 14 that extend from the outside face 8 of the tube in compliance with characteristics that are described below.

In accordance with the invention, each transverse border 13 possesses a sharp edge 16 situated at the intersection between the transverse border 13 and the inside face 7. Each transverse border 13 forms a cutting angle $\alpha$ relative to the inside face 7, with the apex of said angle corresponding to the cutting edge 16. Advantageously, the cutting angle $\alpha$ possesses a value lying in the range 6° to 18°. The two transverse borders 13 extend approximately parallel, facing each other, and presenting cutting zones C that act as knives serving to cut through tissue without tearing, as explained in the description below.

According to an advantageous embodiment characteristic, the cutting edge 16 of each transverse border 13 has two segments $16_1$ converging towards the longitudinal plane L going away from the transverse plane of symmetry T and extending symmetrically relative to the longitudinal plane L. These two converging segments $16_1$ are connected together by a connection segment $16_2$ that is centered on the longitudinal plane L. Said connection segment $16_2$ presents a profile that is different from the profile of the converging segments $16_1$.

In an advantageous variant embodiment, the two converging segments $16_1$ are straight and they are connected together by a connection segment $16_2$ of semicircular or rounded shape. It should be observed that given the circular shape of the tube 2, the profiles of the transverse borders 13 and consequently of the converging and connection segments $16_1$ and $16_2$ do not lie at the same level, but vary in level over a portion of the height of the tube as measured in the longitudinal plane L.

Figure 2:
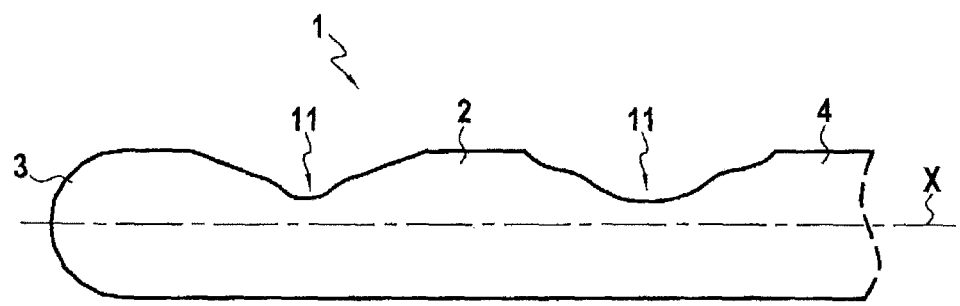
FIG. 2 is a side view of the sampling tool shown in FIG. 1.
Figure 3:
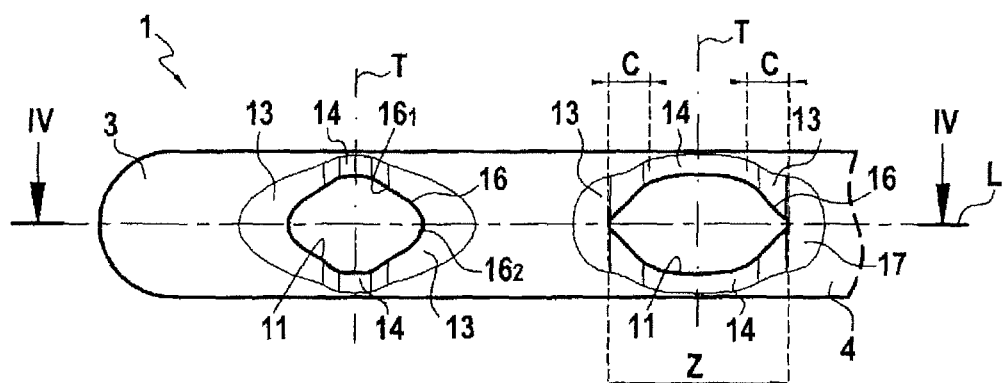
FIG. 3 is a plan view of the sampling tool shown in FIGS. 1 and 2.
Figure 4:
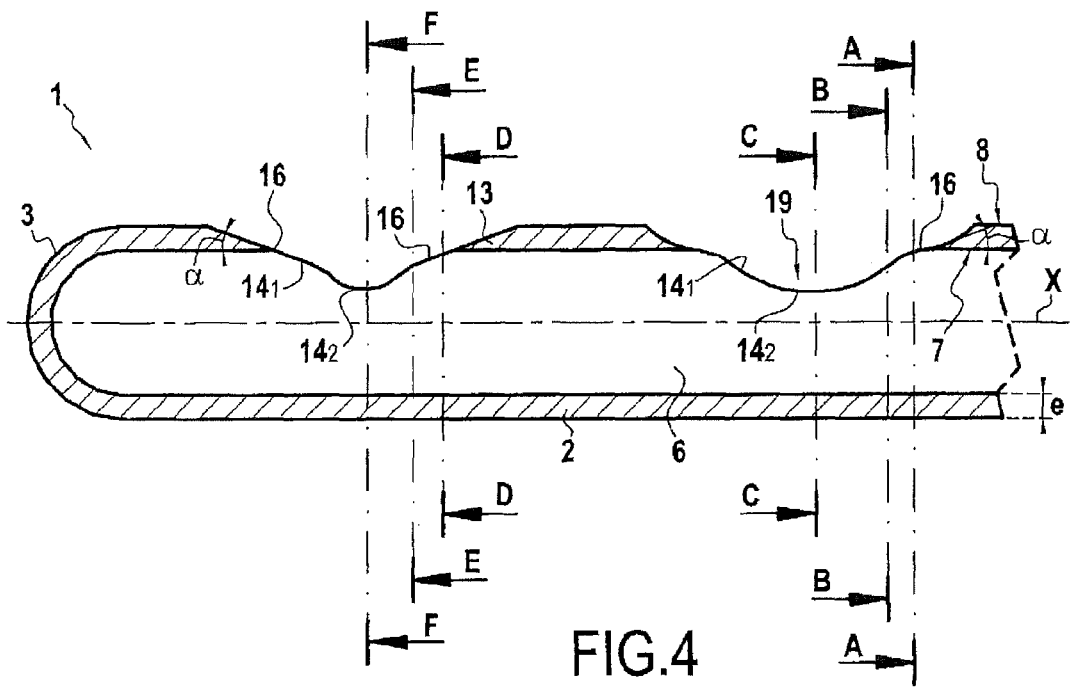
FIG. 4 is an elevation view taken substantially on line IV-IV of FIG. 3.
Figure 5A:
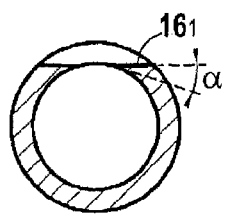
FIGS. 5A to 5C are cross-sections taken respectively on lines A, B, and C of FIG. 4 in one embodiment of a sampling opening.
Figure 5B:
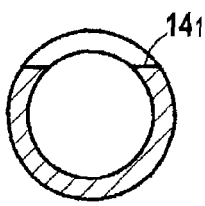
Figure 5C:
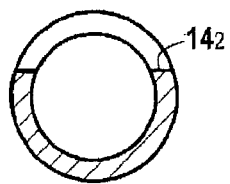
Figure 5D:
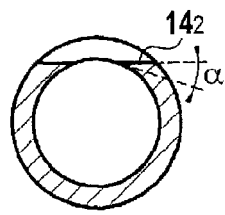
FIGS. 5D to 5F are cross-sections taken respectively on lines D, E, and F of FIG. 4 showing another embodiment of a sampling opening.
Figure 5E:
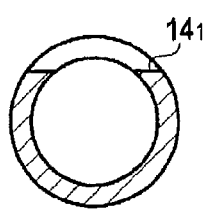
Figure 5F:
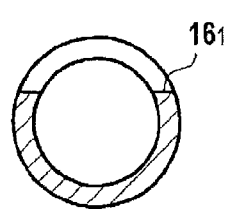

As can be seen more precisely in FIGS. 2 and 4, the transverse borders 13 may present different profiles in the longitudinal plane L. In the drawings, the tube 2 has two sampling orifices 11 with profiles that are different. Thus, for the sampling orifice 11 situated closer to the distal portion 3, each transverse border 13 presents a plane profile in the longitudinal plane L. Concerning the sampling orifice 11 that is situated furthest from the distal portion 3, each transverse border 13 presents a convex profile in the longitudinal plane L. Advantageously, each transverse border 13 is extended in the longitudinal direction and on either side of the longitudinal plane L by a tapering zone 17 that constitutes a bearing surface for adipose tissue.

According to a characteristic of the invention, the two longitudinal borders 14 are arranged in a cup-shape 19 relative to the transverse borders 13, with a profile in the longitudinal plane L that is different from the profile of the transverse borders 13. Each longitudinal border 14 thus possesses a cup-shape 19 situated beyond the transverse border 13 and consequently beyond the cutting edge 16. In other words, there is a profile discontinuity between the transverse borders 13 and the longitudinal borders 14. This profile discontinuity or profile "jump" for the peripheral borders of the sampling orifice 11 contributes to properly positioning adipose tissue inside said orifice, as described below.

Naturally, various profiles may be envisaged for the longitudinal borders 14. Concerning the sampling orifice 11 that is situated closer to the distal portion 3, the profile of each longitudinal border 14 presents two converging curved segments $14_1$ in the longitudinal plane L, which segments are connected together by a straight segment $14_2$ that is parallel to the axis X. Concerning the sampling orifice 11 situated further from the distal end 3, the profile of each longitudinal border 14 presents two converging curved segments $14_1$ in the longitudinal plane L, which segments are connected together by a rounded segment $14_2$.

It should be considered that the cup shape 19 presented by the longitudinal borders 14 serves to position adipose tissue so that it extends inside the channel 6 below the level at which the cutting edges 16 extend. Thus, movement in translation along the direction of the longitudinal axis X leads to adipose tissue being cut cleanly in the adipose tissue trapping zone Z that is situated between the two ends of the orifice 11 as measured in the longitudinal plane L. It should be observed that the adipose tissue may also be in contact with the tapering face 17 while samples are being taken, thereby enhancing the cutting effect on the adipose tissue.

From the above description, it can be seen that the sampling cannula 1 enables tissue to be taken by being cut through by the combined effect of two cutting edges 16 acting as knives on the adipose tissue inserted between the two transverse borders 13. The amount of adipose tissue that is taken is calibrated and depends on the width of the orifice 11, on the length of the orifice 11, on the depth of the orifice 11 as measured in the longitudinal plane L, and also on the profile of the cutting edge 16. In an application of the cannula to a liposuction technique, the channel 6 may be connected to a controlled vacuum suction system such as a syringe or a vacuum source.

The sampling tool 1 of the invention is simple in design, while being relatively easy to use. The sampling tool 1 is in the form of a one-piece tubular element without any moving parts.

In the example shown, the cannula has two sampling orifices 11. Naturally, the cannula of the invention may have some other number of orifices arranged along a generator line of the tube or along two symmetrically-opposed generator lines, or distributed over the entire periphery of the tube, being spaced apart along the length of the tube so as to avoid weakening it.

The invention is not limited to the examples described and shown since numerous modifications may be made thereto without going beyond the ambit of the invention.

What is claimed is:

1. A tissue-sampling tool made in the form of a one-piece tube without any moving parts, the tube presenting an inside face of circular section and an outside face of circular section, the tube having a rounded or hemispherical distal end and at least one sampling orifice extending symmetrically relative to a transverse plane and to a longitudinal plane, the orifice being peripherally bordered by two transverse borders that are symmetrical relative to the transverse plane and that are connected to two longitudinal borders that are symmetrical relative to the longitudinal plane, wherein:

each transverse border possesses a cutting edge situated at the intersection between said borders and the inside face, each transverse border co-operating with the inside face to form a cutting angle lying in the range 6° to 18°; and each transverse border having a bevel surface extending from the cutting edge to an outer surface portion of the one-piece tube, the bevel surface and the inside face forming the cutting angle, and the longitudinal borders are arranged to have a cup-shape relative to the transverse borders, with a profile in the longitudinal plane that is different from the profile of the transverse borders, the difference in the profile of the longitudinal borders and the profile of the transverse borders forming a profile discontinuity, wherein a change in surface orientation occurs where each transverse border and each longitudinal border connect.

2. A sampling tool according to claim 1, wherein the cutting edge of each transverse border comprises two converging segments that are connected together by a connection segment presenting a profile that is different from the profile of the converging segments.

3. A sampling tool according to claim 2, wherein the cutting edge of each transverse border comprises two converging segments connected together by a rounded connection segment.

4. A sampling tool according to claim 1, wherein each transverse border presents a plane profile in the longitudinal plane.

5. A sampling tool according to claim 1, wherein each transverse border presents a convex profile in the longitudinal plane.

6. A sampling tool according to claim 1, wherein each transverse border is extended in the longitudinal direction and on either side of the longitudinal plane by a tapering zone.

7. A sampling tool according to claim 1, wherein the profile of each longitudinal border presents two converging curved segments that are connected together by a straight segment.

8. A sampling tool according to claim 1, wherein the profile of each longitudinal border presents two converging curved segments that are connected together by a rounded segment.

* * * * *